United States Patent
Sunkara et al.

(10) Patent No.: US 11,306,065 B1
(45) Date of Patent: Apr. 19, 2022

(54) CATALYST COMPOSITIONS FOR CONVERSION OF FURFURAL TO 2-METHYLFURAN AND THEIR APPLICATIONS

(71) Applicant: Advanced Energy Materials, LLC, Louisville, KY (US)

(72) Inventors: Mahendra Sunkara, Louisville, KY (US); Sivakumar Vasireddy, Louisville, KY (US); Juan He, Louisville, KY (US); Hugo Apolo Nambo Salgado, Louisville, KY (US)

(*) Notice: Subject to any disclaimer, the term of this patent is extended or adjusted under 35 U.S.C. 154(b) by 0 days.

(21) Appl. No.: 16/703,817

(22) Filed: Dec. 4, 2019

Related U.S. Application Data

(60) Provisional application No. 62/775,150, filed on Dec. 4, 2018.

(51) Int. Cl.
| | |
|---|---|
| *C07D 307/36* | (2006.01) |
| *B01J 23/72* | (2006.01) |
| *B01J 37/34* | (2006.01) |
| *B01J 23/06* | (2006.01) |
| *B01J 21/06* | (2006.01) |
| *B01J 23/80* | (2006.01) |
| *B01J 23/835* | (2006.01) |

(52) U.S. Cl.
CPC .......... *C07D 307/36* (2013.01); *B01J 23/72* (2013.01); *B01J 37/341* (2013.01); *B01J 21/063* (2013.01); *B01J 23/06* (2013.01); *B01J 23/80* (2013.01); *B01J 23/835* (2013.01); *B01J 2219/00029* (2013.01); *B01J 2219/00033* (2013.01)

(58) Field of Classification Search
CPC ....... C07D 307/36; B01J 37/341; B01J 23/72; B01J 23/06; B01J 23/835; B01J 21/063; B01J 2219/00029; B01J 23/80; B01J 2219/00033
See application file for complete search history.

(56) References Cited

U.S. PATENT DOCUMENTS

| | | |
|---|---|---|
| 6,479,677 B1 | 11/2002 | Ahmed |
| 6,852,868 B2 | 2/2005 | Ahmed |
| 7,064,222 B2 | 6/2006 | Ahmed |
| 7,771,689 B2 | 8/2010 | Sunkara et al. |
| 8,168,807 B2 | 5/2012 | Wabnitz et al. |
| 8,324,409 B2 | 12/2012 | Rauchfuss et al. |
| 9,630,162 B1 | 4/2017 | Sunkara et al. |
| 10,030,201 B1 | 7/2018 | Sunkara et al. |
| 10,087,160 B2 | 10/2018 | Chheda et al. |
| 10,189,764 B2 | 1/2019 | Jansen et al. |
| 10,766,787 B1 | 9/2020 | Sunkara et al. |

OTHER PUBLICATIONS

Gandarias, I., "Production of 2-methylfuran from biomass through an integrated biorefinery approach." Fuel Processing Technology 178 (2018): 336-343.*
Srivastava, S., "Copper-cobalt catalyzed liquid phase hydrogenation of furfural to 2-methylfuran: An optimization, kinetics and reaction mechanism study." Chemical Engineering Research and Design 132 (2018): 313-324.*
Fu, Z.,"High efficient conversion of furfural to 2-methylfuran over Ni—Cu/Al2O3 catalyst with formic acid as a hydrogen donor." Applied Catalysis A: General 547 (2017): 248-255.*
Hutchings, G.S.,"Nanoporous Cu—Al—Co alloys for selective furfural hydrodeoxygenation to 2-methylfuran." Industrial & Engineering Chemistry Research 56.14 (2017): 3866-3872.*
Srivastava, S., "A versatile bi-metallic copper-cobalt catalyst for liquid phase hydrogenation of furfural to 2-methylfuran." RSC advances 6.2 (2016): 1649-1658.*

* cited by examiner

*Primary Examiner* — John M Mauro
(74) *Attorney, Agent, or Firm* — Law Office of J L Simunic; Joan Simunic

(57) ABSTRACT

The present development is a method for the selective conversion of furfural to 2-methylfuran (2-MF) using a catalyst comprising non-toxic and non-noble metals and wherein the method requires relatively mild processing conditions. The catalyst comprises copper metal particles, used alone or in combination with cobalt, nickel, manganese, ruthenium, gallium, zinc, aluminum or a combination thereof, on a nanowire support. The catalyst is stable in liquid phase reactions and in the presence of water. The present development also includes a process for producing the catalyst.

13 Claims, 1 Drawing Sheet

CATALYST COMPOSITIONS FOR CONVERSION OF FURFURAL TO 2-METHYLFURAN AND THEIR APPLICATIONS

CROSS-REFERENCE TO PRIOR APPLICATIONS

The present application claims priority to U.S. Patent Application 62/775,150 filed 4 Dec. 2018, which is incorporated by reference in its entirety.

FIELD OF THE INVENTION

The invention relates to catalysts for the conversion of furfural to furans.

BACKGROUND OF THE INVENTION

At present most of our energy and chemical needs are fulfilled from fossil fuels. With growing concerns about diminishing fossil resources, global warming and environmental pollution, the search for renewable resources has attracted worldwide attention. A more promising feedstock is lignocellulose biomass which is abundant, cheaper and potentially more sustainable.

Furfural is considered a main building-block molecule produced from the hemicellulosic fraction of biomass, based on the large variety of products that can be derived from it. Among various products, 2-methylfuran (2-MF) is considered as the most promising gasoline bio-additive based on its suitable fuel properties and its relatively low manufacturing cost and $CO_2$ emissions when produced from furfural. 2-MF has a high octane number (103), higher thermal efficiency than gasoline and it can be directly used in gasoline blends (10 vol %). Despite all its potential, the use of 2-MF as a biofuel or for other chemical applications is hampered by the lack of a technically and economically feasible production process.

The conversion of furfural to 2-methylfuran requires a selective hydrodeoxygenation (HDO) catalyst which selectively cleaves the C—O bond in the aldehyde group of furfural while keeping the C—O bond inside the furan ring intact. Current 2-MF production technologies involve the hydrogenation of furfural using toxic Cu/Cr based and/or expensive noble metal (Pt/Pd) catalysts. Copper Chromite catalyst used in the 2-M F production process has toxicity issues related to chromium and therefore is less desirable from an environmental safety standpoint. Also, the current commercially-available copper catalysts tend to deactivate due to coking and need to be replaced every 2 to 6 months. Noble metal-based catalysts may be used in hydrogenation processes, but these catalysts are non-selective.

Therefore, a catalyst that is chromium free and less susceptible to deactivation would be of commercial interest because it can improve the economics of production of 2-methylfuran from furfural. The critical factors for designing a highly active copper catalyst are: Cu nanoparticle deposition on to a support, high degree of dispersion, and the cooperative effect of $Cu^0$ and $Cu^+$ species. The addition of a second metal, such as Co, can enhance the easier reduction of CuO and has a greater number of active sites which are necessary for hydrogenolysis of in-situ formed furfuryl alcohol to 2-M F.

SUMMARY OF THE PRESENT INVENTION

The present development is a method for the selective conversion of furfural to 2-methylfuran (2-MF) using a catalyst comprising non-toxic and non-noble metals and wherein the method requires relatively mild processing conditions. The catalyst is stable in liquid phase reactions and in the presence of water. The present development also includes a process for producing the catalyst.

More specifically, the method for the hydrogenation of furfural to produce furans such as 2-MF comprises reacting furfural with a hydrogen source in the presence of a copper-based catalyst. The hydrogen source may be hydrogen gas or a hydrogen donor solvent. The catalyst for the reaction comprises copper metal particles (Cu) distributed on a metal oxide nanowire support wherein the copper metal particles have a relatively homogeneous distribution. The catalyst is produced by depositing Cu metal particles, either alone or in combination with other active metal particles, specifically cobalt, nickel, manganese, gallium, ruthenium, zinc, aluminum or a combination thereof, on metal oxide nanowires by plasma oxidation technology or by plasma spray pyrolysis technology. The resulting catalyst converts furfural to 2-MF with enhanced activity and selectivity.

DETAILED DESCRIPTION OF THE PRESENT DEVELOPMENT

Figure 1:
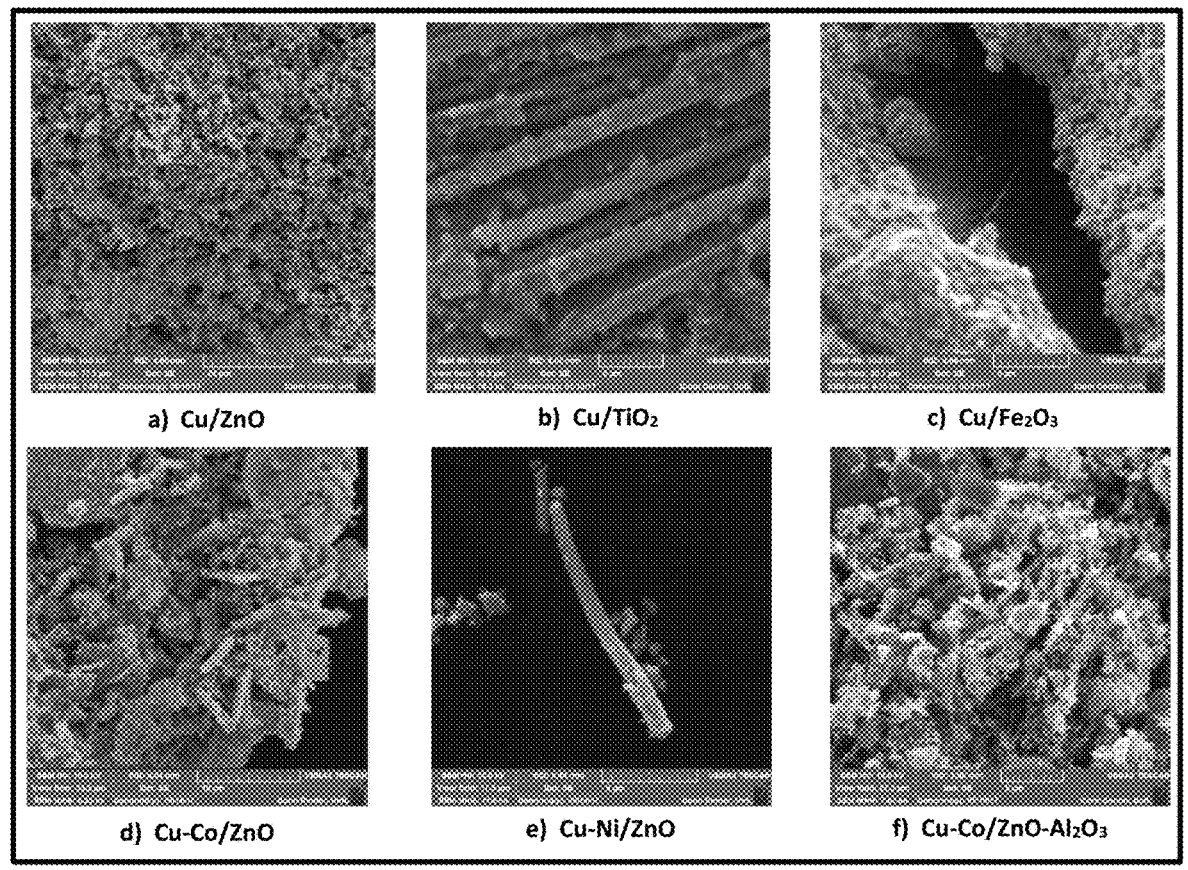
FIG. 1 is a series of scanning electron microscope images of catalytically active metals on nanowires, wherein a) shows copper metal particles on a zinc oxide nanowire, b) shows copper metal particles on a titanium dioxide nanowire, c) shows copper metal particles on an iron oxide nanowire, d) shows copper metal particles and cobalt metal particles on a zinc oxide nanowire, e) shows copper metal particles and nickel metal particles on a zinc oxide nanowire, and f) shows copper metal particles and cobalt metal particles on a zinc oxide-alumina nanowire; and, FIG. 2 is a schematic of the reaction pathways for the hydrogenation of furfural leading to 2-MF and potential byproducts.

The following description is intended to provide the reader with a better understanding of the invention. The description is not intended to be limiting with respect to any element not otherwise limited within the claims. For example, the present invention will be described through a series of examples that have specific compositions, but the teachings herein are not limited to examples provided.

The present development is a method for the hydrogenation of furfural and, more specifically, the selective conversion of furfural to 2-methylfuran (2-MF) using a catalyst comprising copper metal particles (Cu) distributed on a metal oxide nanowire support. The production of 2-MF may be done in a continuous mode fixed bed reactor or batch mode continuous stirred tank reactor. The hydrogenation may be done by pumping gaseous hydrogen into the reactor or by using a hydrogen donor solvent, such as cyclohexanol or isopropanol as a source of hydrogen. The reaction occurs under relatively mild processing conditions, specifically at a hydrogenation reaction temperature of less than 250° C. and an initial hydrogenation reaction pressure of less than 300 psi and a reaction time of less than 8 hours. Some catalyst compositions disclosed herein are effective at hydrogenation reaction temperatures of less than 220° C. Some catalyst compositions disclosed herein are effective at an initial hydrogenation reaction pressure below 50 psi and as low as 8 psi. Some catalyst compositions disclosed herein are effective at reaction times of about 3 hours.

The catalyst for the hydrogenation of furfural comprises a support composed of metal oxide nanowires and catalytically active metal particles secured on the surface or decorating the nanowires. The metal oxide nanowire support preferably comprises titanium oxide, zinc oxide, iron oxide, tin oxide or a combination thereof. Optionally, the support may further comprise alumina.

The catalytically active metals comprise copper metal particles. Optionally, a second or more catalytically active metals may be combined with the copper metal particles. The optional catalytically active metals are selected from cobalt (Co), manganese (Mn), nickel (Ni), zinc (Zn), aluminum (Al), gallium (Ga), ruthenium (Ru) and combinations thereof. In the finished catalyst composition, the catalytically active metals may be in the form of elemental metal, metal oxide, mixed metal oxides, mono- or bi- or tri-metallic oxide alloy nanoparticles or combinations thereof.

To prepare the catalyst of the present invention the catalytically active metals may also be provided in the form of precursors, wherein the precursors for catalytically active particles are metal nitrates or metal acetates or metal carbonates. Exemplary monometallic catalysts anticipated by the present invention include Cu metal decorated onto the nanowire support, such as but not limited to Cu/ZnO, $Cu/TiO_2$, $Cu/Fe_2O_3$, $Cu/ZnO$—$Al_2O_3$. As used herein, bimetallic catalysts refer to bimetallic alloys or mixed oxides containing Cu and second metal selected from the group consisting of Zn, Mn, Ni, Co, Ru and Ga. Representative examples of bimetallic catalysts anticipated by the present invention include Cu metal plus a second metal decorated onto the nanowire support, such as but not limited to Cu—Co/ZnO, Cu—Ni/ZnO, Cu—Mn/ZnO, Cu—Ga/ZnO, Cu—Co/ZnO—$Al_2O_3$, Cu—Ru/ZnO, Cu—Co/$Fe_2O_3$, Cu—Co/$TiO_2$, Cu—Ni/$Fe_2O_3$, Cu—Co/$TiO_2$—$Al_2O_3$, Cu—Ni/$TiO_2$—$Al_2O_3$. In a preferred embodiment, the bimetallic catalyst has the composition $Cu_{1-x}M_xO$ (x=0-0.5) wherein M=Co, Mn, Ni, Ga, Ru. As used herein, trimetallic catalysts refer to trimetallic alloy or trimetallic mixed oxides having Cu, a second metal selected from the group consisting of Zn, Mn, Ni, Co, Ru and Ga, and a third metal selected from the group consisting of Al and Zn. Representative examples of trimetallic catalysts anticipated by the present invention include Cu metal plus a second metal plus a third metal decorated onto the nanowire support, such as but not limited to Cu—Zn—Al/ZnO, Cu—Co—Al/ZnO, Cu—Co—Zn/ZnO, Cu—Mn—Zn/ZnO, Cu—Ni—Al/$Fe_2O_3$. In a preferred embodiment, the trimetallic catalyst has the composition $Cu_xM_yN_{1-x-y}O$ (x=0-0.5; y=0-0.5) wherein M=Co, Mn, Ni, Ga, Ru and N=Zn, Al.

Loading of the catalytically active metals may vary from about 1 wt % to about 20 wt %. In a preferred embodiment, copper metal is loaded onto the nanowire support at a concentration of from about 3 wt % to about 20 wt %, and more preferably at a concentration of from about 6 wt % to about 15 wt %, and most preferably at a concentration of about 12 wt %. If a second catalytically-active metal is used, the second catalytically-active metal is loaded onto the nanowire support at a concentration of up to about 12 wt %, and more preferably at a concentration of from about 4 wt % to about 8 wt %, and most preferably at a concentration of about 6 wt %. If a second catalytically-active metal is used, the third catalytically-active metal is loaded onto the nanowire support at a concentration of up to about 12 wt %, and more preferably at a concentration of from about 4 wt % to about 8 wt %, and most preferably at a concentration of about 6 wt %. In a preferred embodiment, the active metal decorated nanowire has a homogeneous dispersion of metal particles. In a more preferred embodiment, the catalyst is a bimetallic catalyst or a trimetallic catalyst and the active metal decorated nanowire has a homogeneous dispersion of metal particles and has a maximum number of active sites as demonstrated with a BET surface area equal to or greater than 1 $m^2/g$.

The catalysts of the present invention may be prepared by any means known to decorate nanowires with catalytically active metal particles, including but not limited to impregnation techniques or by plasma oxidation techniques or by plasma spray pyrolysis techniques or by solvo plasma techniques. For example, the catalysts may be prepared by obtaining the metal oxide nanowires and loading the selected catalytically active metals onto the nanowires via wet impregnation or incipient wetness techniques, as is known in the art. The wet impregnation method involves loading the catalytically active metals onto the nanowires by mixing metal oxide nanowires with a solution of the selected metal precursors dissolved in deionized water. The incipient wetness or dry impregnation process involves mixing the metal oxide nanowires powder with a solution of the selected metal precursors dissolved in deionized water at a volume equivalent to the pore volume of the nanowires. The water is then evaporated in an oven held at a temperature between 80° C. to 150° C., more preferably between 100° C. and 120° C. The time of drying is between 6 h-20 h, more preferably between 10 h-15 h. The dried material is then calcined in a furnace at 350° C.-500° C., more preferably between 400° C.-450° C. for 2 h-6 h. Scanning electron microscope images of representative catalysts of the present invention prepared by the incipient wetness process are shown in FIG. 1, wherein a)-c) show monometallic catalysts with copper metal particles on a zinc oxide support and on a titanium dioxide support and on an iron oxide nanowire, respectively, and wherein d)-f) show bimetallic catalysts with copper metal particles mixed with cobalt metal particles on a zinc oxide nanowire, and copper metal particles mixed with nickel metal particles on a zinc oxide nanowire, and copper metal particles mixed with cobalt metal particles on a zinc oxide-alumina nanowire, respectively.

Alternatively, the catalyst for the hydrogenation of furfural can be prepared using a plasma oxidation method. Metal oxide nanowires (ZnO and $TiO_2$) are mixed with catalytically active metal precursors (metal nitrates, acetates or carbonates) and deionized water to form a paste, and then the paste is exposed to microwave plasma radiation for from about 15 sec to about 120 sec, and more preferably between about 40 sec and about 80 sec. The usage of plasma eliminates the drying and calcination steps which are energy intensive and have high process times. The plasma oxidation method is recommended for catalysts comprising bimetallic alloy nanoparticles supported on nanowires.

Catalytically active bimetallic or trimetallic oxide alloy nanoparticles having the composition $Cu_xM_yN_{1-x-y}O$ (M-Co, Mn, Ni; N-Zn, Al) and x=0-0.5, y=0-0.5 can also be prepared using plasma spray pyrolysis. This method involves preparing an aqueous solution of a mixture of metal precursors, such as metal nitrates, metal acetates or metal carbonates, and then injecting the metal precursor solution into a plasma flame or hydrocarbon flame. Plasma spray pyrolysis experiments were performed in an air plasma flame using an upward atmospheric microwave plasma flame (atmospheric plasma) with power ranging from of 750 to 1200 W and variable exposure times (from about 30 seconds to about five minutes). In a typical experiment, precursor solution is injected into the plasma flame. Direct exposure is a more intensive process wherein the sample itself is faced directly toward the plasma flame having closer interaction with the oxidative species and the flame, allowing faster heating and higher radical concentrations. The method results in a precisely controlled composition of alloy nanoparticles. These catalytically active alloy nanoparticles can either be mixed with metal oxide nanowires ($TiO_2$, ZnO, $SnO_2$ and/or $Al_2O_3$) or used in the as-synthesized form.

Alternatively, catalytically active bimetallic alloy nanowires having the composition $Cu_xM_yN_{1-x-y}O$ (M-Co, Mn, Ni; N-Zn, Al) and x=0-0.5, y=0-0.5 can be prepared by synthesizing CuO nanowires using a solvo-plasma method as described in U.S. Pat. No. 9,409,141 and US 2018/0187094, both of which are incorporated by reference in their entireties, and then mixing the nanowires with an aqueous solution of a mixture of metal precursors, and then thermally treating the metal precursor coated nanowires in a furnace under vacuum and/or an inert atmosphere at temperatures of from about 450° C. to about 700° C. for from about 1 hour to about 6 hours, more preferably from about 2 hour to about 4 hours. In a preferred embodiment, the metal precursors are metal nitrates, metal acetates, metal carbonates or a combination thereof. The catalytically active alloy nanowires may be used as synthesized or they may be mixed with $Al_2O_3$, $TiO_2$, and/or ZnO supports.

The metal oxide nanowires are prepared by methods known in the art. A preferred method to produce zinc oxide nanowires is taught by Sunkara et al. in US Published Application 2012/0027955, which is incorporated herein in its entirety by reference. Iron oxide nanowires may be synthesized by thermal oxidation of iron metal, techniques that are known in the art. Preferred temperatures for thermal oxidation range from 700° C. to 800° C. for a period of from about 2 hours to about 8 hours. In a most preferred embodiment the thermal oxidation is performed at about 750° C. for about 4 hours.

The following examples are provided to enhance the reader's understanding of the invention and are not intended to be limiting with respect to any element not otherwise limited within the claims:

Catalyst Examples 1-11 (Table 1) are prepared by the following general procedure: The catalytically active metal source is dissolved in deionized $H_2O$ to produce an active metal solution. The nanowire powder is then added dropwise to the active metal powder solution while stirring to form a paste. Stirring is continued for about 20 min after the active metal solution is completely added. The mixture of nanowire powder and active metal solution is dried in an oven held at about 120° C. for approximately 15 hours. The dried product is transferred to a furnace and the furnace temperature is raised from room temperature to about 450° C. at a heating ramp of about 5° C. $min^{-1}$ and the dried product is then calcined in the furnace held at about 450° C. for about 3 h in static air. The catalyst properties are characterized by X-ray diffraction, scanning electron microscopy, and Hz-temperature programmed reduction, and BET surface area and pore volumes measured by $N_2$ adsorption/desorption isotherms at its liquefaction temperature are reported for some of the example catalysts.

TABLE 1

| | Example | | | | | |
|---|---|---|---|---|---|---|
| | 1 | 2 | 3 | 4 | 5 | 6 |
| Catalyst | Cu/ZnO | Cu/TiO$_2$ | Cu/Fe$_2$O$_3$ | bimetallic | bimetallic | bimetallic |
| Catalyst composition | 10% Cu—90% ZnO | 10% Cu—90% TiO$_2$ | 10% Cu—90% Fe$_2$O$_3$ | 12% Cu—6% Co—82% ZnO | 12% Cu—6% Ni—82% ZnO | 12% Cu—12% Co—76% TiO$_2$ |
| Nanowire powder used | 9 g ZnO | 9 g TiO$_2$ | 9 g Fe$_2$O$_3$ | 8.2 g ZnO | 8.2 g ZnO | 7.6 g TiO$_2$ |
| Copper source (added as powder) | 3.14 g copper(II) acetate | 3.14 g copper(II) acetate | 3.14 g copper(II) acetate | 3.64 g copper(II) nitrate pentahydrate | 3.64 g copper(II) nitrate pentahydrate | 3.64 g copper(II) nitrate pentahydrate |
| 2$^{nd}$ Active metal source | none | none | none | 2.18 g cobalt(II) nitrate hexahydrate | 3.5 g nickel nitrate hexahydrate | 4.35 g cobalt(II) nitrate hexahydrate |
| 3$^{rd}$ Active metal source | none | none | none | none | none | none |
| DI water volume to disperse active metal powders | 16 ml | 16 ml | 16 ml | 30 ml | 30 ml | 30 ml |
| BET Surface area (m$^2$/g$_{cat}$) | 8.5 | 7.8 | 2.0 | 10 | 7 | n/a |
| XRD phase | CuO, ZnO | CuO | CuO, Fe$_2$O$_3$ | CuO, ZnO, Co$_3$O$_4$ | CuO, ZnO, Ni$_{0.75}$Cu$_{0.25}$O | n/a |

| | Example | | | | | |
|---|---|---|---|---|---|---|
| | 7 | 8 | 9 | 10 | 11 | |
| Catalyst | bimetallic | bimetallic | bimetallic | bimetallic | trimetallic | |
| Catalyst composition | 12% Cu—12% Co—76% (80% ZnO—20% Al$_2$O$_3$) | 5% Cu—5% Ga—90% ZnO | 12% Cu—6% Mn—82% (80% ZnO—20% Al$_2$O$_3$) | 12% Cu—6% Co—82% (ZnO—Al$_2$O$_3$) | 12% Cu—6% Co—6% Zn—76% (80% ZnO—20% Al$_2$O$_3$) | |
| Nanowire powder used | 12.6 g ZnO 3.04 g Al$_2$O$_3$ | 9 g ZnO | 12.6 g ZnO 3.04 g Al$_2$O$_3$ | 6.56 g ZnO 1.64 g Al$_2$O$_3$ | 6.08 g ZnO 1.52 g Al$_2$O$_3$ | |
| Copper source (added as powder) | 7.29 g copper(II) nitrate | 0.95 g copper(II) nitrate | 7.29 g copper(II) nitrate | 3.64 g copper(II) nitrate | 3.64 g copper(II) nitrate | |
| 2$^{nd}$ Active metal source | 8.70 g cobalt(II) nitrate | 1.30 g gallium nitrate | 3.47 g manganese(II) nitrate | 2.18 g cobalt(II) nitrate | 2.18 g cobalt(II) nitrate hexahydrate | |
| 3$^{rd}$ Active metal source | none | none | none | none | 2.19 g Zn(II) nitrate hexahydrate | |
| DI water volume to disperse active metal powders | 7 ml | 7.7 ml | 7 ml | 7 ml | 7 ml | |
| BET Surface area (m$^2$/g$_{cat}$) | n/a | n/a | n/a | 90 | n/a | |
| XRD phase | n/a | n/a | n/a | Cu$_{0.5}$Co$_{1.5}$O$_4$ | n/a | |

Example 12: A monometallic catalyst of the present invention comprising $Cu_{0.09}Zn_{0.91}O$ is prepared using the plasma oxidation method by dispersing about 8.8 g of ZnO nanowires into an aqueous solution containing about 3.65 g of copper(II) nitrate making it as a paste. The paste is then spread on a quartz slide and exposed it to the upward microwave based atmospheric plasma. The time of exposure to plasma is about 60 s.

Example 13: A bimetallic catalyst of the present invention comprising $Cu_{0.08}Co_{0.08}Zn_{0.82}O$ is prepared as described in Example 12, except about 7.6 g of ZnO nanowires powder dispersed in a solution containing about 4.35 g of cobalt(II) nitrate and about 3.64 g of copper(II) nitrate and about 15 ml of deionized $H_2O$.

Example 14: A bimetallic alloy catalyst of the present invention comprising $Cu_{0.08}Co_{0.08}Zn_{0.82}O$ is prepared using the plasma spray pyrolysis method by mixing about 4.35 g of cobalt(II) nitrate, about 3.64 g of copper nitrate, about 29.97 g of zinc nitrate and about 60 ml of deionized $H_2O$. The solution is then sprayed through a nozzle onto a highly dense oxygen rich microwave plasma discharge with a vertically upward flow confined in a conical cavity. The micron size droplets, when sprayed into hot oxygen plasma, instantly oxidizes and solidifies upon exiting the flame region. The resulting powder is then collected in a bag house filter.

Figure 2:
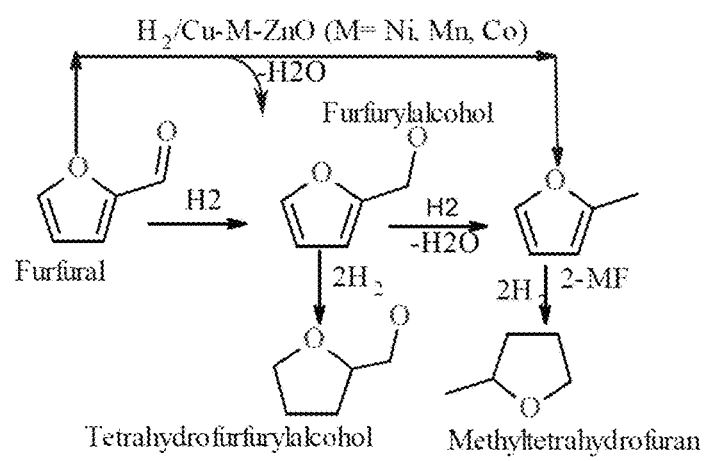

The catalyst of the present invention may be used in the hydrogenation of furfural to produce furans such as 2-MF. The production of 2-MF may be done in a continuous mode fixed bed reactor or batch mode continuous stirred tank reactor by hydrogenation of furfural in presence of a catalyst. The hydrogenation may be done by pumping gaseous hydrogen into the reactor or using a hydrogen donor solvent such as cyclohexanol or isopropanol as a source of hydrogen. The furfural may be mixed with a solvent and feed onto the catalyst bed in a fixed bed reactor or by using a mixture of furfural, solvent and catalyst in a stirred tank reactor. A schematic showing the reaction pathways for the hydrogenation of furfural leading to 2-MF and potential byproducts is shown in FIG. 2.

The hydrogenation of furfural to 2-MF is conducted in a 50 ml volume autoclave reactor. The hydrogenation involves feeding the autoclave with furfural. Optionally, the reactants may be diluted with solvent, preferably cyclohexanol or isopropanol. The autoclave is charged with the catalyst. The autoclave is then flushed with $N_2$ gas for about 1 h and then with $H_2$ gas for about another 1 h. The reactor is heated to about 230° C.-300° C., more preferably between 250° C.-270° C., with a $H_2$ gas flow to reduce the catalyst. The rate of heating is between 2° C. $min^{-1}$ and 10° C. $min^{-1}$, preferable about 5° C. $min^{-1}$, and the reduction time is from about 1 h to about 6 h, more preferably from about 2 h to about 4 h. The reactor is then cooled to room temperature and then charged with furfural and solvent. The reactor temperature is then raised to a hydrogenation temperature of between about 180° C. to about 250° C., and the pressure is adjusted with $H_2$ gas. The rate of heating is between 2° C. $min^{-1}$ and 5° C. $min^{-1}$. The $H_2$ and $N_2$ gas flows are controlled by mass flow controllers. The autoclave is continuously under stirring during hydrogenation. The hydrogenation is continued for about 1 h-12 h to achieve high conversion and selectivity. The reactants and the reaction products are analyzed by gas chromatogram with mass spectroscopy and flame ionization detector.

Examples 15-20: The hydrogenation of furfural to 2-MF is conducted in an autoclave in the presence of monometallic or bimetallic catalysts prepared using the impregnation technique as described for Examples 1-11 and using cyclohexanol solvent. The hydrogenation experiments are conducted at a temperature of about 220° C., for about 3 h of reaction time and at a pressure of about 145 psi. The amount of catalyst is about 0.2 g and reactant quantities are about 3 ml furfural and about 30 ml cyclohexanol. The other byproducts include 2-methyl tetrahydrofuran, tetrahydrofuran, furan, and tetrahydrofurfuryl alcohol. The results are summarized in Table 2.

TABLE 2

| | | | | Selectivity % | | |
|---|---|---|---|---|---|---|
| Example | Solvent | Catalyst | conversion % | 2-MF | Furfuryl alcohol | Others |
| 15 | cyclohexanol | 10% Cu—90% $Fe_2O_3$ | 100 | 11.6 | 37.8 | 50.6 |
| 16 | cyclohexanol | 10% Cu—90% $TiO_2$ | 92 | 11.9 | 6.6 | 81.4 |
| 17 | cyclohexanol | 10% Cu—90% ZnO | 100 | 18.4 | 52.7 | 28.9 |
| 18 | cyclohexanol | 12% Cu—6% Co—82% ZnO | 91.8 | 26.5 | 50 | 23.5 |
| 19 | cyclohexanol | 12% Cu—6% Ni—82% ZnO | 100 | 6.6 | 54.4 | 39 |
| 20 | cyclohexanol | 5% Cu—5% Ga—90% ZnO | 100 | 4.4 | 69.5 | 26.1 |

Examples 21-33: The hydrogenation of furfural to 2-MF follows the same method as described in Example 15, except isopropanol is used as a solvent and reaction conditions are reaction time of about 4 h and pressure equal to about 100 psi. The amount of catalyst is about 1.0 g and reactant quantities are about 3.7 ml furfural and about 20 ml isopropanol. The conversion and selectivity results are summarized in Table 3.

TABLE 3

| | | | | Selectivity % | | |
|---|---|---|---|---|---|---|
| Example | Solvent | Catalyst | conversion % | 2-MF | Furfuryl alcohol | Others |
| 21 | Isopropanol | 10% Cu—90% $TiO_2$ | 63.8 | 0 | 100 | 0 |
| 22 | Isopropanol | 10% Cu—90% ZnO | 59.3 | 0 | 95.2 | 4.8 |
| 23 | Isopropanol | 10% Cu—90% FeO | 58.3 | 1.8 | 76.2 | 21.9 |

TABLE 3-continued

| Example | Solvent | Catalyst | conversion % | Selectivity % 2-MF | Furfuryl alcohol | Others |
|---|---|---|---|---|---|---|
| 24 | Isopropanol | 12% Cu—12% Co—76% ZnO | 83.3 | 1.4 | 76 | 22.6 |
| 25 | Isopropanol | 12% Cu—12% Co—76% $TiO_2$ | 61.2 | 0 | 100 | 0 |
| 26 | Isopropanol | 12% Cu—6% Co—82% ZnO | 78.6 | 1.7 | 73.3 | 25.0 |
| 27 | Isopropanol | 12% Cu—12% Co—76% ZnO | 83.3 | 1.4 | 76 | 22.6 |
| 28 | Isopropanol | 12% Cu—6% Mn—82% (ZnO—$Al_2O_3$) | 100 | 1 | 78.2 | 20.8 |
| 29 | Isopropanol | 12% Cu—6% Co—6% Mn—76% (ZnO—$Al_2O_3$) | 100 | 5.5 | 63.4 | 31.0 |
| 30 | Isopropanol | 12% Cu—6% Co—6% Zn—76% (ZnO—$Al_2O_3$) | 100 | 44.0 | 22.6 | 33.3 |
| 31 | Isopropanol | 12% Cu—12% Co—12% Zn—64% $Al_2O_3$ | 100 | 63.5 | 1.4 | 35.1 |
| 32 | Isopropanol | 12% Cu—12% Co—76% $Al_2O_3$ | 100 | 66.7 | 0 | 33.3 |
| 33 | Isopropanol | 12% Cu—12% Co—76% (ZnO—$Al_2O_3$) | 100 | 52 | 12 | 36 |

Examples 34-35: The furfural hydrogenation using catalyst 12% Cu-12% Co-76% (ZnO—$Al_2O_3$) is carried out as described in Example 21, except the hydrogenation reaction temperature is varied from 220° C. to 250° C. and/or the initial hydrogenation reaction pressure is varied between 10 psi to 300 psi and/or the reaction time is varied between 3 h and 8 h, as indicated in Table 4. The hydrogenation test results are summarized in Table 4.

TABLE 4

| Example | Catalyst | conversion % | Selectivity % 2-MF | Furfuryl alcohol | Others | Temperature (° C.) | Initial Pressure (psi) | Reaction Time hr |
|---|---|---|---|---|---|---|---|---|
| 34 | 12% Cu—12% Co—76% (ZnO—$Al_2O_3$) | 100 | 48.6 | 31.8 | 19.6 | 220 | 100 | 3 |
| 35 | 12% Cu—12% Co—76% (ZnO—$Al_2O_3$) | 100 | 36.0 | 0 | 64.0 | 250 | 100 | 3 |
| 36 | 12% Cu—12% Co—6% Zn—70% (ZnO—$Al_2O_3$) | 100 | 82.2 | 0 | 17.8 | 220 | 10 | 4 |
| 37 | 12% Cu—12% Co—6% Zn—70% (ZnO—$Al_2O_3$) | 100 | 30.7 | 29.9 | 39.4 | 220 | 100 | 4 |
| 38 | 12% Cu—12% Co—6% Zn—70% (ZnO—$Al_2O_3$) | 95.3 | 14.4 | 34.1 | 51.5 | 220 | 200 | 4 |
| 39 | 12% Cu—12% Co—6% Zn—70% (ZnO—$Al_2O_3$) | 100 | 19.9 | 21.1 | 59 | 220 | 300 | 4 |
| 40 | 12% Cu—12% Co—76% (ZnO—$Al_2O_3$) | 100 | 48.6 | 31.8 | 19.6 | 220 | 100 | 3 |
| 41 | 12% Cu—12% Co—76% (ZnO—$Al_2O_3$) | 100 | 52 | 12 | 36 | 220 | 100 | 4 |
| 42 | 12% Cu—12% Co—6% Zn—70% (ZnO—$Al_2O_3$) | 100 | 30.7 | 29.9 | 39.4 | 220 | 100 | 4 |
| 43 | 12% Cu—12% Co—6% Zn—70% (ZnO—$Al_2O_3$) | 100 | 33.3 | 0 | 66.7 | 220 | 100 | 8 |

The catalyst may be used in a fixed bed reactor for the continuous production of 2-MF by hydrogenating furfural. For this application, the catalyst is plugged between quartz wool in a glass reactor. The reactor is then flushed with $N_2$ gas followed by a $H_2$ gas flow. The catalyst is first reduced in the $H_2$ gas flow at 250° C. for 4 h and then the reactor temperature s adjusted to the desired temperature, preferably between about 180° C. and about 250° C. Furfural is pumped onto the catalyst bed along with $H_2$ gas and the flow rate is controlled by syringe infusion pump and mass flow controller. A solvent may be used, but is not required. The reaction product mixture is analyzed by gas chromatogram with mass and flame ionization detectors.

Examples 44-50: The furfural hydrogenation is carried out as described in Example 21, except the catalysts of Examples 44-45 and 48 are prepared using the plasma oxidation method described for Example 12 and the catalysts of Examples 46-47 and 49-50 are prepared using the plasma spray pyrolysis method described for Example 14, and for Examples 44-50 the initial hydrogenation reaction pressure is varied between 8 psi to 50 psi, as indicated in Table 5. The hydrogenation test results are summarized in Table 5.

TABLE 5

| Example | Catalyst | Initial Pressure (psi) | Conversion % | Selectivity % 2-MF | Furfuryl alcohol | Others |
|---|---|---|---|---|---|---|
| 44 | 18% ($Cu_{0.5}Co_{0.5}O_x$)/82% (ZnO—$Al_2O_3$) | 50 | 99.3 | 67.2 | 31.4 | 1.4 |
| 45 | 24% ($Cu_{0.5}Co_{0.5}O_x$)/76% $Al_2O_3$ | 50 | 100 | 81.3 | 2.9 | 15.7 |
| 46 | 36% ($Cu_{0.33}Co_{0.33}Zn_{0.33}O_x$)/64% $Al_2O_3$ | 50 | 100 | 87.7 | 3.9 | 8.3 |
| 47 | 36% ($Cu_{0.33}Co_{0.33}Zn_{0.33}O_x$)/64% $Al_2O_3$ | 15 | 98.2 | 84.6 | 5.5 | 9.9 |
| 48 | 18% ($Cu_{0.5}Co_{0.5}O_x$)/82% (ZnO—$Al_2O_3$) | 8 | 98.7 | 94.7 | 2.2 | 3.1 |
| 49 | 30% ($Cu_{0.4}Co_{0.4}Zn_{0.2}O_x$)/70% (ZnO—$Al_2O_3$) | 10 | 100 | 82.2 | 0 | 17.8 |
| 50 | 24% ($Cu_{0.5}Co_{0.25}Zn_{0.25}O_x$)/76% (ZnO—$Al_2O_3$) | 10 | 100 | 82.9 | 7.4 | 9.6 |

As demonstrated by the examples, the bimetallic alloy catalysts prepared by plasma oxidation demonstrate a higher selectivity in the production of 2-MF (94%) than catalysts having similar compositions but prepared by impregnation. The liquid phase hydrogenation of furfural to 2-MF occurs under relatively mild processing conditions, i.e. T<220° C. and initial pressure<20 psi, with 100% furfural conversion and 94% selectivity to 2-MF. Without being bound by theory, it is believed the increased activity can be attributed either to an increase of metal electron density or the creation of new active sites, which both favor the hydrogenation of the C=O group and eliminate undesirable reactions, such as decarbonylation and ring opening.

The catalysts of the present invention are non-precious Cu-based bimetallic catalysts. The method of making the catalysts generates little to no secondary waste, thereby making the catalyst product environmentally-friendly. The bimetallic $Cu_xM_yZn_{1-x-y}O$ (wherein M=Co, Ni, Mn) nanowires are made by plasma spray pyrolysis which produces homogeneous dispersion with controlled composition of alloys and maximum number of active sites. The bimetallic alloy nanoparticles having the composition $Cu_{1-x}M_xO$ (wherein M=Co, Ni, Mn) are prepared by plasma oxidation and are supported on porous nanowire oxides $TiO_2$ and ZnO. The addition of a co-promoter, such as Zn, has been shown to improve the intrinsic activity of the catalyst. Further, the catalyst is recyclable with sustained activity and selectivity.

Unless defined otherwise, all technical and scientific terms used herein have the same meaning as commonly understood by one of ordinary skill in the art to which the presently disclosed subject matter pertains. Representative methods, devices, and materials are described herein, but are not intended to be limiting unless so noted.

The terms "a", "an", and "the" refer to "one or more" when used in the subject specification, including the claims. The term "ambient temperature" as used herein refers to an environmental temperature of from about 0° F. to about 120° F., inclusive.

Unless otherwise indicated, all numbers expressing quantities of components, conditions, and otherwise used in the specification and claims are to be understood as being modified in all instances by the term "about". Accordingly, unless indicated to the contrary, the numerical parameters set forth in the instant specification and attached claims are approximations that can vary depending upon the desired properties sought to be obtained by the presently disclosed subject matter.

As used herein, the term "about", when referring to a value or to an amount of mass, weight, time, volume, concentration, or percentage can encompass variations of, in some embodiments ±20%, in some embodiments ±10%, in some embodiments ±5%, in some embodiments ±1%, in some embodiments ±0.5%, and in some embodiments to ±0.1%, from the specified amount, as such variations are appropriate in the disclosed application.

All compositional percentages used herein are presented on a "by weight" basis, unless designated otherwise.

What is claimed is:

1. A method for the selective conversion of furfural to 2-methylfuran (2-MF) comprising:
    (a) providing a catalyst comprising copper metal particles and a metal oxide nanowire support wherein the catalyst is formed by plasma oxidation of a paste formed by mixing precursors of the copper metal particles with the metal oxide nanowire support;
    (b) loading a reactor with the catalyst;
    (c) reducing the catalyst;
    (d) cooling the reactor to room temperature;
    (e) feeding a hydrogen source and furfural into the reactor;
    (f) heating the reactor to a predetermined temperature between 180° C. and 250° C.;
    (g) pressuring the reactor to a predetermined pressure of less than 300 psi;
    (h) allowing the furfural to react with the hydrogen source in the presence of the catalyst for a reaction time of less than 12 hours; and,
    (i) recovering 2-methylfuran from the reactor.

2. The method of claim 1 wherein the catalyst further comprises active metal particles selected from the group consisting of cobalt, nickel, manganese, gallium, ruthenium, zinc, aluminum and combinations thereof, and wherein precursors of the active metal particles are mixed with the precursors of the copper metal particles and with the metal oxide nanowire support to form the paste.

3. The method of claim 2 wherein the metal oxide nanowire support comprises titanium oxide, zinc oxide, iron oxide, tin oxide, alumina or a combination thereof.

4. The method of claim 1 wherein the metal oxide nanowire support comprises titanium oxide, zinc oxide, iron oxide, tin oxide, alumina or a combination thereof.

5. The method of claim 1 wherein the hydrogen source is hydrogen gas or cyclohexane or isopropanol.

6. The method of claim 1 wherein the reaction pressure is between 8 psi and 100 psi.

7. The method of claim 1 wherein the reaction uses a continuous mode fixed bed reactor or batch mode continuous stirred tank reactor.

8. A method for the selective conversion of furfural to 2-methylfuran (2-MF) comprising:
    (a) providing a catalyst having a composition $Cu_xM_yN_{1-x-y}O$ wherein M=Co, Mn, Ni and N=Zn, Al and x=0-0.5 and y=0-0.5;
    (b) loading a reactor with the catalyst;
    (c) reducing the catalyst;
    (d) cooling the reactor to room temperature;
    (e) feeding a hydrogen source and furfural into the reactor;
    (f) heating the reactor to a predetermined temperature between 180° C. and 250° C.;
    (g) pressuring the reactor to a predetermined pressure of less than 300 psi;
    (h) allowing the furfural to react with the hydrogen source in the presence of the catalyst for a reaction time of less than 12 hours; and,
    (i) recovering 2-methylfuran from the reactor.

9. The method of claim 8 wherein the catalyst is prepared by plasma spray pyrolysis.

10. The method of claim 9 wherein the catalyst is mixed with metal oxide nanowires selected from the group consisting of $TiO_2$, ZnO, $SnO_2$, $Al_2O_3$, and combinations thereof.

11. The method of claim 8 wherein the reaction uses a continuous mode fixed bed reactor or batch mode continuous stirred tank reactor.

12. The method of claim 8 wherein the hydrogen source is hydrogen gas or cyclohexane or isopropanol.

13. The method of claim 8 wherein the reaction pressure is between 8 psi and 100 psi.

* * * * *